United States Patent [19]

Motooka

[11] Patent Number: 4,472,633
[45] Date of Patent: Sep. 18, 1984

[54] METHOD AND APPARATUS OF MEASURING CARRIER DISTRIBUTION

[75] Inventor: Teruaki Motooka, Yamanashi, Japan

[73] Assignee: Hitachi, Ltd., Tokyo, Japan

[21] Appl. No.: 344,975

[22] Filed: Feb. 2, 1982

[30] Foreign Application Priority Data

Feb. 9, 1981 [JP] Japan ................................. 56-17012

[51] Int. Cl.³ ........................................... G01N 21/21
[52] U.S. Cl. ..................................... 250/338; 250/341
[58] Field of Search ..................... 250/338, 341, 358.1; 356/369

[56] References Cited

U.S. PATENT DOCUMENTS 3,426,201  2/1969  Hilton et al. ......................... 250/338
3,623,818  11/1971  Gardner et al. ..................... 356/369
4,030,836  6/1977  Smith .................................. 356/369

Primary Examiner—Janice A. Howell
Assistant Examiner—Constantine Hannaher
Attorney, Agent, or Firm—Antonelli, Terry & Wands

[57] ABSTRACT

A semiconductor wafer is irradiated with a linearly polarized infrared light beam. On the basis of changes in the polarized state of the light reflected from the wafer, the distribution of the density of carriers depthwise in the wafer is determined. Distribution of the carrier density in the semiconductor wafer can be measured very rapidly in a contactless manner without destroying the wafer.

7 Claims, 10 Drawing Figures

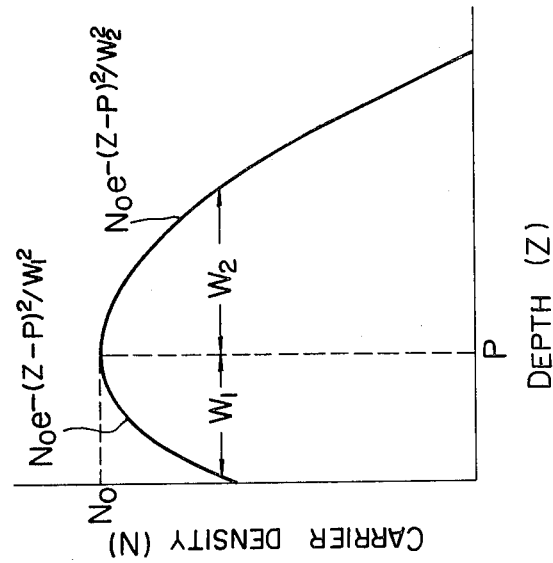
FIG. 6
FIG. 5
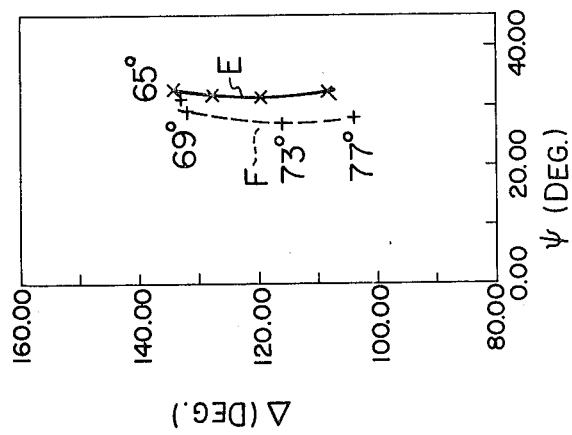
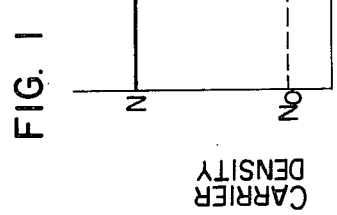
FIG. 1
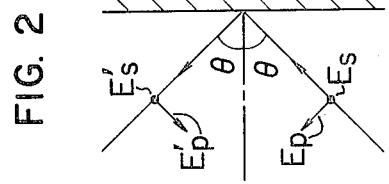
FIG. 2

METHOD AND APPARATUS OF MEASURING CARRIER DISTRIBUTION

The present invention relates generally to a method and an apparatus of measuring the distribution of the density of carriers in a wafer. In particular, the invention concerns a method and an apparatus of measuring the carrier distribution depthwise of a wafer in a contactless and non-destructive manner.

In view of the fact that carrier depth distribution in a silicon wafer is a fundamental parameter characterizing a semiconductor device implemented in the wafer, it is very important to measure the carrier depth distribution in the silicon wafer with high accuracy.

Heretofore, in the measurement of the carrier depth distribution in a silicon wafer, there has been most widely adopted a method according to which a silicon wafer is oxidized up to a predetermined depth through anodic oxidation or anodization and subsequently an oxide film thus formed is etched away or stripped to estimate the quantity of carriers contained in the etched region by suitable means such as by measuring the Hall coefficient of the wafer substrate in a repetitional manner.

However, the hitherto known method in which etching and estimation have to be repeatedly effected is extremely troublesome. Besides, the wafer used in the measurement undergoes destruction due to the etching and can be used no more for manufacturing a semiconductor device but must be scrapped.

As other methods of measuring the carrier distribution, there have been proposed numerous methods, e.g., sputter-etching alternated with measurement of resistance (Japanese Patent Application Laid-Open No. 41953/1976), irradiation of a wafer with radiant ray and generation of charged particles from carriers through nuclear reaction (Japanese Patent Application Laid-Open No. 72568/1977), formation of a plurality of semiconductor metal Schottky junctions by making continuously varying the thickness of a wafer (Japanese Patent Application Laid-Open No. 153096/1979) and others. However, all of these prior art methods are disadvantageous in that operations or manipulations required in the measurements are very delicate, troublesome and time-consuming and that the measurements are poor in accuracy, rendering it extremely difficult to carry out the methods for practical applications. Such being the circumstances, there has been a great demand for a method which allows the measurement of carrier depth distribution in a wafer to be effected in a contactless manner with a high accuracy without involving destruction of the wafer.

An object of the present invention is to solve the problems of the hitherto known methods and provide a method and an apparatus which are capable of measuring the depth distribution of carriers in a wafer in a much facilitated manner without involving destruction of the wafer.

In view of the object, it is proposed according to a feature of the invention that a surface of a wafer is irradiated with linearly polarized infrared-light, wherein the carrier distribution in the wafer is determined by measuring changes in the polarized state of the light reflected from the wafer surface.

The invention will now be described by way of example with reference to the accompanying drawings, in which:

FIGS. 1 and 6 show schematic diagrams to illustrate carrier distribution profiles in wafers;

FIG. 2 illustrates schematically electric field components with incident and reflected light;

Figure 3:
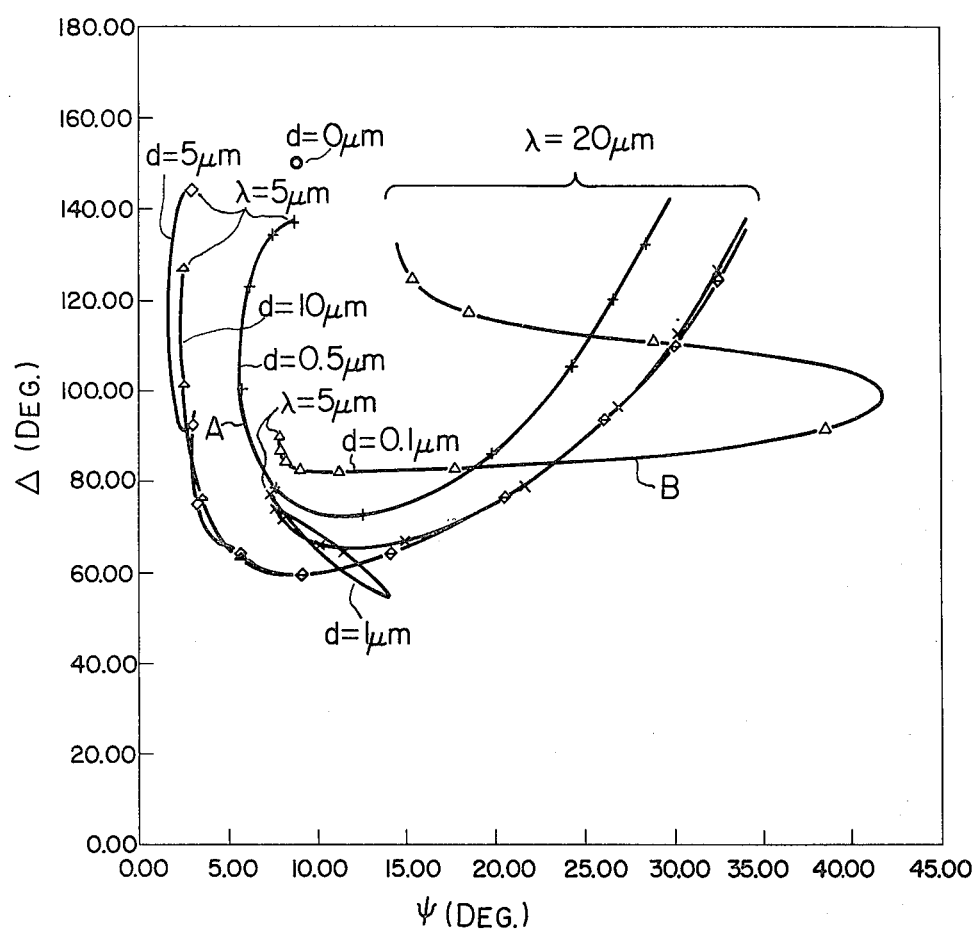
Figure 4:
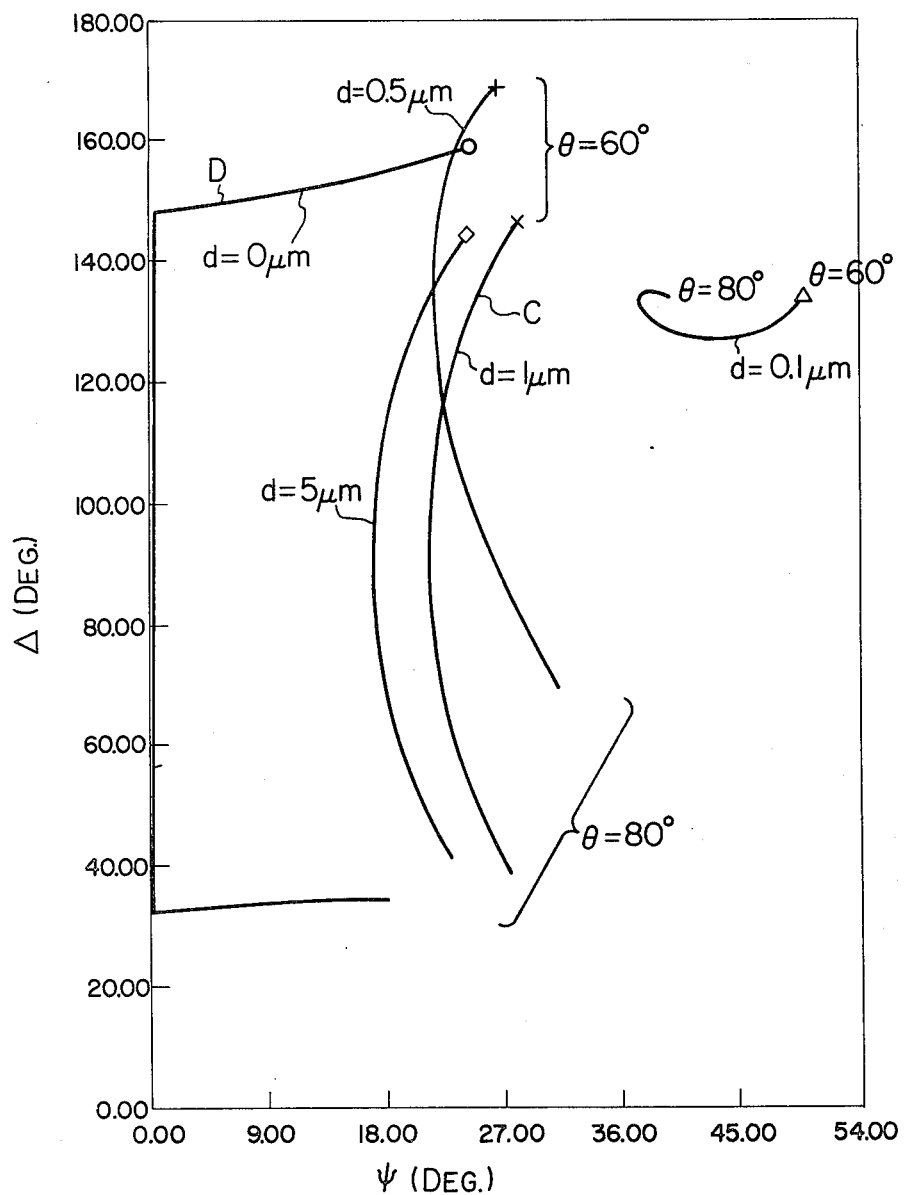
Figure 7:
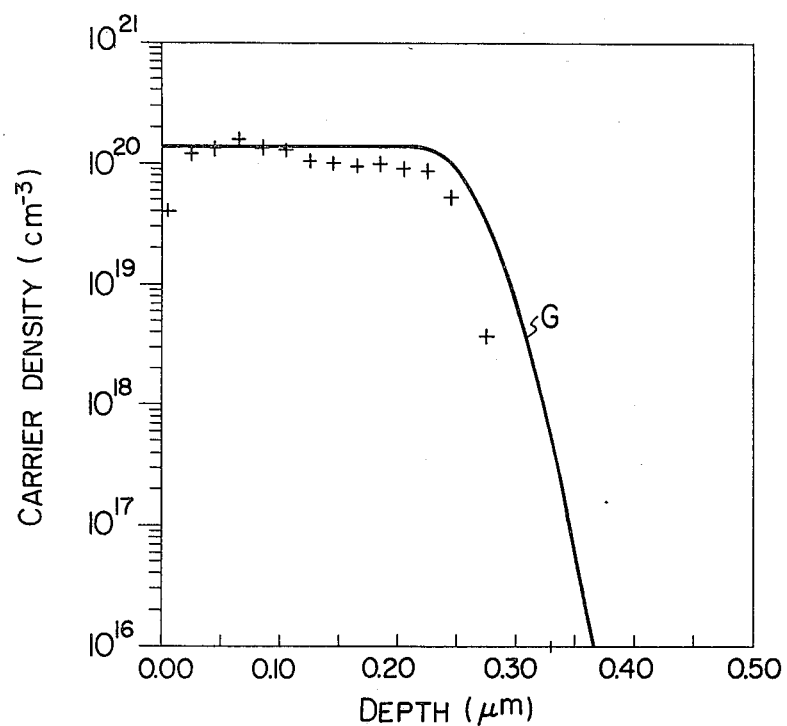
Figure 8:
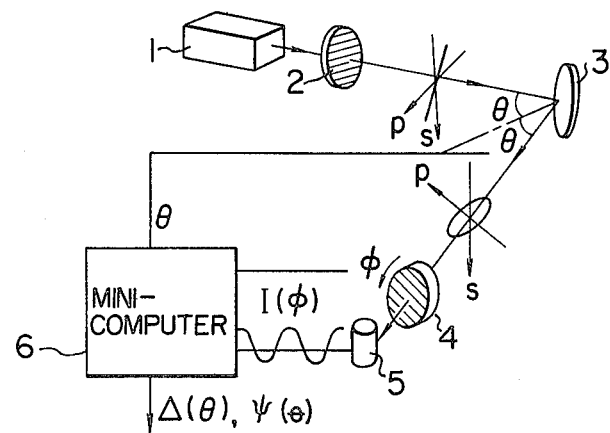
Figure 9:
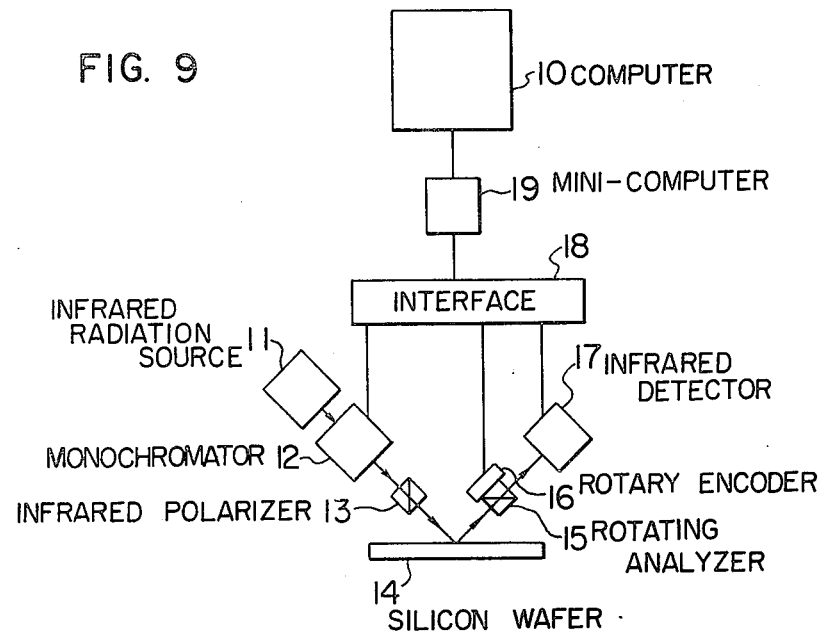
Figure 10:
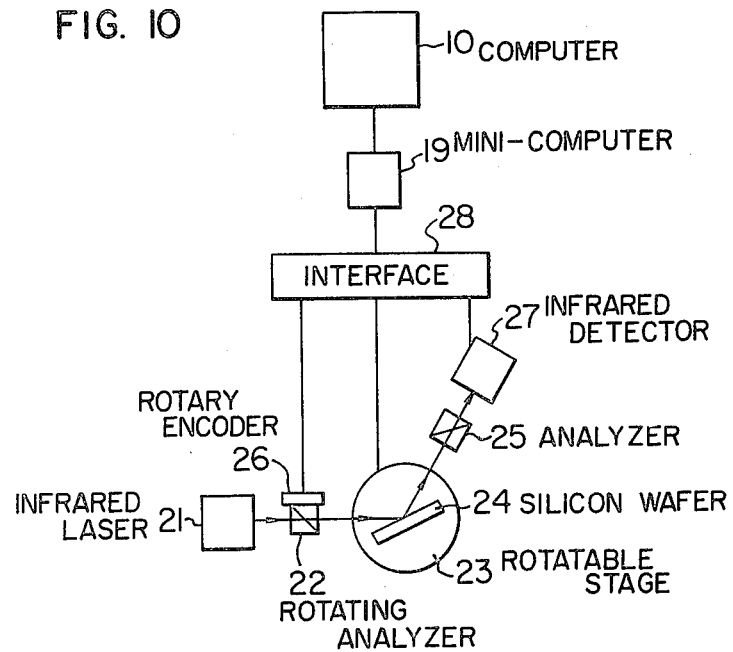

FIGS. 3 and 4 graphically show $\Delta$-$\psi$ curves as obtained (through calculation) when the wavelength and the incident angle of incident light are varied, respectively;

FIG. 5 shows a schematic diagram to illustrate a method according to an exemplary embodiment of the invention;

FIG. 7 graphically shows distribution of carriers as measured by a method according to an exemplary embodiment of the invention;

FIG. 8 illustrates schematically a manner in which the method according to the invention can be carried out; and FIGS. 9 and 10 illustrate schematically other various manners in which the method according to the invention can be carried out.

FIG. 1 schematically shows a profile of carrier distribution in a silicon wafer on the simplest assumption.

Referring to the figure, it will be seen that the density of carriers takes a predetermined constant value in a depth range of 0 to d, while in a region deeper than the depth d, the carrier density takes value $N_o$ inherent to a wafer. In general, the depth d is referred to as a junction depth.

Consideration will be made on the assumption that linearly polarized monochromatic light is projected at an incident angle of $\theta$ onto a surface of the wafer which has the carrier distribution illustrated in FIG. 1. Referring to FIG. 2, when s- and p-polarization components of the electric field with incident light are represented by $E_s$ and $E_p$, respectively, while s- and p-polarization components of the electric field with reflected light are represented, respectively, by $E'_s$ and $E'_p$, the following relation (1) connects the electric field components of the incident and the reflected light. That is, $$\begin{pmatrix} E'_s \\ E'_p \end{pmatrix} = \begin{pmatrix} r_s e^{i\phi_s} & 0 \\ 0 & r_p e^{i\phi_p} \end{pmatrix} \begin{pmatrix} E_s \\ E_p \end{pmatrix} \quad (1)$$

where $r_p$ and $r_s$ represent absolute values of complex reflection amplitudes of the p- and s-polarization components, respectively, and $\phi_p$ and $\phi_s$ represent, respectively, changes in the phase of the p- and s-components occurring upon reflection.

Accordingly, the terms $r_p e^{i\phi_p}$ and $r_s e^{i\phi_s}$ of Eq. (1) represent the complex reflective amplitudes of p- and s-polarized light, respectively.

Since $r_p$, $r_s$, $\phi_p$ and $\phi_s$ are determined in dependence on the dielectric constant $\epsilon(\omega)$ of a material of the wafer where $\omega$ represents the angular frequency of the incident light, it can be said that the quantities $r_p$, $r_s$, $\phi_p$ and $\phi_s$ reflect properties of the material through the dielectric constant $\epsilon(\omega)$ serving as a parameter.

On the other hand, when a surface of a given material is irradiated with a linearly polarized monochromatic light and the varied state of polarization (generally elliptical polarization) of the reflected light is measured, quantities $\Delta$ and $\psi$ defined by the following expression (2) can be determined. That is, $$\tan \psi = r_p/r_s, \text{ and } \Delta = \phi_p - \phi_s \quad (2)$$

The measurement based on this principle is commonly referred to as ellipsometry, while a measuring instrument employed in the measurement is referred to as an ellipsometer. Thus, by measuring the quantities $\Delta$ and $\psi$ through ellipsometry, data or information concerning the dielectric constant $\epsilon(\omega)$ of the concerned material at the angular frequency $\omega$ can be obtained. In particular, when the material as measured exhibits homogeneity or uniformity depthwise, the dielectric constant $\epsilon(\omega)$ can be determined on the basis of the quantities $\Delta$ and $\psi$ in accordance with the following expression (3):

$$\epsilon(\omega) = \sin^2\theta \tan^2\theta \left(\frac{1-\rho}{1+\rho}\right)^2 + \sin^2\theta \quad (3)$$

where $\rho = \tan \psi^{i\Delta}$.

The dielectric constant $\epsilon(\omega)$ consists of two terms $\epsilon_b(\omega)$ and $\epsilon_f(\omega)$, as given by the following expression (4):

$$\epsilon(\omega) = \epsilon_b(\omega) + \epsilon_f(\omega) \quad (4)$$

The term $\epsilon_b(\omega)$ corresponds to the interband transition and is substantially independent of the carriers. On the other hand, the term $\epsilon_f(\omega)$ significantly depends on the carrier density.

For this reason, it is required to obtain the component $\epsilon_f(\omega)$ to determine the carrier distribution. In this connection, it is noted that for visible and ultraviolet light, $\epsilon_b(\omega) >> \epsilon_f(\omega)$. Accordingly, the use of these light rays is not suitable for carrying out the invention. In contrast, for infrared light, the component $\epsilon_b(\omega)$ considerably decreases so that $\epsilon_f(\omega) >> \epsilon_b(\omega)$ and thus can be practically neglected.

It is thus preferred for effecting the method according to the invention to employ the infrared light as the incident light which permits much information about the carriers to be made available.

The relation between the carrier distribution $N(Z)$ and the dielectric constant component $\epsilon_f(\omega, Z)$ is given by the expression (5) mentioned below on the assumption that $N(Z)$ represents the carrier densities $N$ at depths $Z$ and $\epsilon_f(\omega, Z)$ represents the dielectric constant of the material at angular frequency $\omega$ at depth $Z$.

$$\epsilon_f(\omega, Z) = \epsilon_\infty - \frac{4\pi N(Z)e^2}{m^*\omega^2} \cdot \frac{1}{1 + i/\omega\tau} \quad (5)$$

where
- $\epsilon_\infty$: dielectric constant for non-doped Si,
- $m^*$: carrier effective mass,
- $\tau$: carrier relaxation time,
- $\omega$: angular frequency of incident light, and
- $e$: electron charge.

Thus, by measuring the quantities $\Delta$ and $\psi$ through ellipsometry by using infrared light, information about the dielectric constant component $\epsilon_f(\omega, Z)$ can be obtained. Further, information about the carrier distribution $N(Z)$ can be derived in accordance with expression (5).

Here, it must be mentioned that the dielectric constant component $\epsilon_f(\omega, Z)$ usually exhibits different values in the depth direction. However, the expression (3) can be only applied to the homogeneous material. It is thus impossible to determine the dielectric constant $\epsilon_f(\omega, Z)$ straight-forwardly from the expression (3).

In the light of the above, it is taught according to the invention that measurement of the quantities $\Delta$ and $\psi$ through the infrared ellipsometry is repeated while varying successively the angular frequency $\omega$ or the angle of incidence $\theta$ of the incident infrared light, to thereby determine a plurality of values of the quantities $\Delta$ and $\psi$ in a range of appropriate values of the angular frequency $\omega$ or the incident angle $\theta$.

After experimental examinations conducted by the inventor of the present application, it has been found that, when a $\Delta$-$\psi$ curve is plotted on the basis of the plural measurement values obtained through ellipsometry as mentioned above, the carrier distribution $N(Z)$ can be determined with the aid of the $\Delta$-$\psi$ curve, since the curve is in one-to-one correspondence with the carrier distribution, as can be seen from the several curves shown in FIGS. 3 and 4.

More particularly, there are shown in FIG. 3 the $\Delta$-$\psi$ curves which are plotted on the basis of the calculated results of the ellipsometric measurements conducted on a silicon wafer at the junction depths d of 0, 0.1, 0.5, 1, 5 and 10 $\mu$m, which wafer has a profile of carrier distribution similar to the one illustrated in FIG. 1 and has the carrier density N of $5 \times 10^{19}$ cm$^{-3}$. In the measurement, the incident angle $\theta$ of the infrared light is fixed at 70°, while the wavelength $\lambda$ (where $\lambda = 2\pi C/\omega$ and C represents velocity of light) of the incident infrared light is successively changed from 5 to 20 $\mu$m, whereby changes in the quantities $\Delta$ and $\psi$ are determined for plotting the $\Delta$-$\psi$ curves.

At both ends of each of the $\Delta$-$\psi$ curves, there are inserted "$\lambda = 5$ $\mu$m" and "$\lambda = 20$ $\mu$m", respectively, which mean that these ends of the curve represent the values of $\Delta$ and $\psi$ with wavelengths $\lambda$ of 5 $\mu$m and 20 $\mu$m, respectively. In other words, each of the $\Delta$-$\psi$ curves represents changes in $\Delta$ and $\psi$ as the wavelength $\lambda$ of the incident infrared light is varied successively from 5 $\mu$m to 20 $\mu$m.

For example, curve A shown in FIG. 3 represents variations in the quantities $\Delta$ and $\psi$ plotted on the basis of the results of calculation obtained on the assumption that the wavelength $\lambda$ of the linearly polarized infrared light impinging on a silicon wafer, which has a profile of carrier distribution shown in FIG. 1, the junction depth d of 0.5 $\mu$m and the carrier density N of $5 \times 10^{19}$ cm$^{-3}$, is varied in the range from 5 $\mu$m to 20 $\mu$m. In a similar manner, curve B shown in FIG. 3 represents variations in $\Delta$ and $\psi$ obtained through calculation made under the same conditions except that the junction depth d is 0.1 $\mu$m. Further, FIG. 4 shows the $\Delta$-$\psi$ curves obtained by calculation for silicon wafers exhibiting the sample profile of carrier distribution as the one used for plotting the curves shown in FIG. 3 and having the junction depths d of 0, 0.1, 0.5, 1 and 5 $\mu$m, respectively. In this case, however, the wavelength of the incident infrared light is assumed to be fixed at 10.6 $\mu$m, while the incident angle $\theta$ is successively varied from 60° to 80° for determining variations in the quantities $\Delta$ and $\psi$. In FIG. 4, there are inserted at both ends of each of the $\Delta$-$\psi$ curves "$\theta = 60°$" and "$\theta = 80°$", respectively, which means that the values of $\Delta$ and $\psi$ at the angles of incidence $\theta$ of 60° and 80°, respectively, take the corresponding end values.

For example, curve C shown in FIG. 4 represents variations in the values of $\Delta$ and $\psi$ determined by calculation in the case in which a silicon wafer having the profile of carrier distribution shown in FIG. 1, the junction depth d of 1 $\mu$m and the carrier density N of $5 \times 10^{19}$ cm$^{-3}$ is assumed to be irradiated with linearly polarized infrared light of the wavelength λ of 10.6 μm with the incident angle θ being successively varied in the range of 60° to 80°.

When the junction depth d equals zero (d=0), the values of Δ and ψ undergo no changes independent of variation in the wavelength λ, as can be seen in FIG. 3. In contrast, when the incident angle θ is varied with the wavelength λ of the incident light being fixed, the quantities Δ and ψ undergo variations, as is represented by curve D.

As will be understood from the foregoing, the Δ-ψ curves are in one-to-one correspondence with the carrier distributions. Accordingly, by preparing previously a number of the Δ-ψ curves corresponding to respective carrier distributions and comparing them with the Δ-ψ curve plotted on the basis of the actual measurements of the infrared ellipsometry, it is possible to determine the carrier distribution N(Z) in concern from the Δ-ψ curve (previously prepared through calculation) to which the ellipsometrically determined Δ-ψ curve approximates most closely.

In the following, description will be made of an example in which the carrier distribution is determined by measuring through ellipsometry. The changes or variations in the values of Δ and ψ occur when the incident angle θ is successively varied with the wavelength λ of the incident infrared light being fixed.

In this example, a p-type (100) silicon wafer having a resistivity of 10 Ω.cm was implanted with As+ ions at a dose of $5 \times 10^{15}$ cm$^{-2}$ at an energy of 80 Kev and subsequently annealed at 1000° C. for 40 minutes to form a heavily doped region in the wafer surface. The carrier distribution was measured in the manner mentioned below.

In the first place, the wafer surface was irradiated with a linearly polarized infrared light having a wavelength λ of 10.6 μm with the incident angle θ being varied from 65° to 77° successively by an increment of 4°, and the quantities Δ and ψ were measured through ellipsometry. The measured values are indicated in FIG. 5 by symbols "+".

On the other hand, a model of carrier distribution which is one of the most typical distribution profiles as shown in FIG. 6 was established.

As can be seen from FIG. 6, the carrier distribution N(Z) is composed of a Gaussian distribution $N_o e^{-(Z-P)^2/w_1^2}$ corresponding to a region where $Z \leq P$ and a Gaussian distribution $N_o e^{-(Z-P)^2/w_2^2}$ in a region where $Z \leq P$. Accordingly, by determining the four parameters $N_o$, P, $w_1$ and $w_2$ (of which $N_o$ represents the maximum density, P represents the depth of the maximum density, and $w_1$ and $w_2$ represent the widths of the respective Gaussian distributions), it is possible to determine the shape of the curve shown in FIG. 6, i.e. the carrier distribution N(Z).

For determining the four parameters $N_o$, P, $w_1$ and $w_2$ from the measured values of Δ and ψ, a number of the Δ-ψ curves are plotted on the basis of the results of calculations made for various values of the four parameters $N_o$, P, $w_1$ and $w_2$ and compared with the Δ-ψ curve plotted on the basis of the measured values of Δ and ψ. The four parameters $N_o$, P, $w_1$ and $w_2$ may then be determined from the calculated Δ-ψ curve which best approximates the measured Δ-ψ curve.

Detailed procedure is as follows. A set of the parameters of distribution ($N_o$, P, $w_1$ and $w_2$) can be given by a single point in a four-dimensional space. For each point the calculated values $\Delta_{cal}(\theta)$ and $\psi_{cal}(\theta)$ of Δ and ψ corresponding to each of the incident angle θ can be determined by solving the Maxwell's equations.

In the case of the present example, the angle of incidence θ was selected at 65°, 69°, 73° and 77°, as described above.

For determining among a number of combinations of the distribution parameters $N_o$, P, $w_1$ and $w_2$ mentioned above the optimum parameters which conform most closely to the experimentally determined values of Δ and ψ, the calculated values $\Delta_{cal}(\theta_i)$ and $\psi_{cal}(\theta_i)$ of Δ and ψ which approximate most closely to experimentally determined values $\Delta_{exp}(\theta_i)$ and $\psi_{exp}(\theta_i)$ of Δ and ψ corresponding to the incident angles $\theta_i$ (where $\theta_1 = 65°$, $\theta_2 = 69°$, $\theta_3 = 73°$ and $\theta_4 = 77°$) are to be found to thereby determine the corresponding distribution parameters $N_o$, P, $w_1$ and $w_2$.

Approximation or "deviation" between the experimentally or ellipsometrically determined values and the calculated values of Δ and ψ can be evaluated with the aid of a quantity η which is defined by the following expression (6):

$$\eta = \underset{1 \leq i \leq 4}{\text{Max}} \left[ |\Delta_{exp}(\theta_i) - \Delta_{cal}(\theta_i)|, |\psi_{exp}(\theta_i) - \psi_{cal}(\theta_i)| \right] \quad (6)$$

As will be seen from the above expression (6), the quantity η represents the maximum value of difference between the experimentally determined values and the calculated values of Δ and ψ. It is thus obvious that the optimum distribution parameters ($N_o$, P, $w_1$ and $w_2$) can be found by determining the values of $\Delta_{cal}(\theta_i)$ and $\psi_{cal}(\theta_i)$ which minimize the quantity η.

When the ranges in which the optimum distribution parameters are to be searched are defined such that $N_o$ is in the range of $10^{17}$ to $10^{21}$ cm$^{-3}$, P is of 0 to 5 μm, $w_1$ is of 0 to 10 μm and that $w_2$ is in the range of 0 to 10 μm, a certain region corresponding to these ranges is defined in the four-dimensional space. First, a number of points, usually 20 or 30, are randomly distributed in the region. Then, three points are arbitrarily selected for use in calculating the η value in accordance with the expression (6). Among the three selected points, the two points having larger values of the quantity η are connected by a straight line. A reflecting or symmetry point of the other one relative to the straight line is determined, and subsequently the value of η at the reflection point is calculated.

The value of η at the reflection point thus obtained is compared with the values of η at the other two points. Then, the point having the greatest value of η is eliminated from the three points. By repeating this procedure, the points having large values of the quantity η are successively eliminated from the group of points which are randomly distributed in the region described above, whereby convergence is made to the points having smaller and smaller values of η, and finally the point having the minimum value of η is attained. This final point of convergence corresponds to the optimum distribution parameters.

The quantities $\Delta_{cal}(\theta_i)$ and $\psi_{cal}(\theta_i)$ corresponding to the point derived in this manner are indicated by symbols "X" in FIG. 5.

From FIG. 5, it will be noted that a curve E passing through a series of the calculated values "X" comes relatively close to coinciding with a curve F plotted through the measured values "+".

The values of the distribution parameters $N_o$, P, $w_1$ and $w_2$ which correspond to the $\Delta$-$\psi$ curve E mentioned above are as follows:

$N_o = 1.3 \times 10^{20}$ cm$^{-3}$
P = 0.23 μm,
$w_1 = 5.0$ μm, and
$w_2 = 0.098$ μm.

On the basis of the distribution parameters of the above values, a carrier distribution N(Z) of the profile illustrated in FIG. 7 is determined. More specifically, a curve G shown in FIG. 7 represents the carrier distribution determined in accordance with the teaching of the invention, while a series of symbols "+" represent a carrier distribution determined according to the hitherto known method in which wafer material is progressively etched away by a predetermined quantity and the quantity of carriers is successively estimated, as described hereinbefore.

As is apparent from the graphical representation of FIG. 7, the carrier distribution determined in accordance with the invention coincides well with the results obtained by the hitherto known measuring method. It is thus confirmed that the method according to the invention allows the carrier distribution depthwise in a silicon wafer to be rapidly measured without destroying the wafer.

By the way, determination of the carrier distribution according to the invention requires a relatively large number of calculations. However, these can be executed in a facilitated manner by resorting to the known procedure of computer fitting, whereby the measurement of the carrier distribution can be carried out at a significantly high speed as compared with the hitherto known methods.

Next, an exemplary manner in which the invention may be carried out will be described.

FIG. 8 shows schematically a fundamental arrangement of an exemplary system for realizing the invention.

Referring to FIG. 8, a monochromatic infrared light emitted by a light source 1 which may be, for example, a $CO_2$-laser is linearly polarized by a polarizer 2 and impinges onto a silicon wafer 3 at an incident angle $\theta$.

A light ray or beam reflected by the silicon wafer 3 impinges onto an infrared detector 5 after having passed through a rotating analyzer 4.

The incident angle $\theta$, rotation angle $\phi$ of the rotating analyzer 4 and output signal I($\phi$) from the infrared detector 5 are supplied to a mini-computer 6 and utilized for calculating or arithmetically determining the values of $\Delta(\theta)$ and $\psi(\theta)$ corrresponding to the incident angle $\theta$.

The values of $\Delta(\theta)$ and $\psi(\theta)$ thus determined are then inputted to a computer (not shown) of a large scale as compared with the mini-computer 6, whereby the corresponding carrier distribution is determined through the calculations described hereinbefore. The calculations as required can be executed rapidly in accordance with the known computer fitting procedure.

FIG. 9 shows schematically an arrangement of another exemplary system for carrying out the invention.

A light ray or beam emitted from an infrared radiation source 11 which may be, for example, a tungsten filament lamp, a black body radiation source or the like is converted into a monochromatic light beam by a monochromator 12 and subsequently linearly polarized by an infrared polarizer 13 to impinge onto a surface of a silicon wafer 14.

The light beam reflected from the surface of the silicon wafer 14 is detected by an infrared detector 17 by way of a rotating analyzer 15.

Setting of the wavelength λ of the monochromator 12 is commanded by a mini-computer 19 through an interface 18. On the other hand, the detected signal output from the detector 17 and an angle signal produced by a rotary encoder 16 are supplied to the mini-computer 19 through the interface 18.

Processing of measured values $\Delta(\lambda)$ and $\psi(\lambda)$ is executed by the mini-computer 19 with resultant data being processed by a large scale computer 10 to determine the carrier distribution. It goes without saying that the processing by the computer 10 may be effected by a system of conversational type or through batch processing.

FIG. 10 shows schematically an arrangement of an exemplary system for carrying out the invention in which a silicon wafer is irradiated with an infrared light beam at different incident angles to determine the carrier distribution.

Referring to FIG. 10, a laser light beam emitted from an infrared laser 21 which may be, for example, a $CO_2$-laser, a semiconductor laser or the like impinges onto a silicon wafer 24 by way of a rotating polarizer 22 at the incident angle $\theta$ which can be set to a desired value by means of a rotatable stage 23 moved under command of a mini-computer 19.

An analizer 25 and an infrared detector 27 are mounted on an arm (not shown) which is interlocked with the rotatable stage 23.

The detection signal output from the detector 27 is supplied to a mini-computer 19 together with an angle signal from a rotary encoder 26 through an interface 28. The processing of the measured values of $\Delta(\theta)$ and $\psi(\theta)$ may, of course, be effected in the manner described hereinbefore.

As will be appreciated from the foregoing description, the invention has now proposed a method which is capable of measuring the carrier density depthwise in wafers in a contactless manner without destroying the wafer in a much facilitated operation or manipulation manner and provides great advantages and contribution in the relevant industrial field.

In Table 1, there are listed the results of measurements obtained according to the invention for comparison with those of the prior art methods, i.e. anodization and etching or stripping method and capacitance measuring method. In the case of both prior art methods, the silicon wafers are inevitably destroyed in addition to a lot of time required for the measurement. In contrast, the method according to the invention allows the measurement in a contactless manner without destroying wafers and with an accuracy of at least the same degree as that of the prior art methods.

TABLE 1

|  |  | Range of measurement Density (cm$^{-3}$) Depth (μm) | Resolution Depth (μm) Area (mm$\phi$) | Turn around time | Remarks |
|---|---|---|---|---|---|
| Prior art | Anodization stripping | $10^{16}$–5 × $10^{20}$ 0–10 | ~0.05 ~10 | 4–5 (hours) | Destructive |

TABLE 1-continued

| | | Range of measurement Density (cm$^{-3}$) Depth (μm) | Resolution Depth (μm) Area (mmφ) | Turn around time | Remarks |
|---|---|---|---|---|---|
| Invention | Capacitance method | $10^{15}$–$10^{18}$ 0.2–10 | ~0.01 ~1 | 4–5 (hours) | Destructive |
| | Polarization of reflected light | $10^{17}$–$5 \times 10^{20}$ 0–10 | ≦0.01 ≦1 | ≦15 (minutes) | Non-contacted and Non-destructive |

In the foregoing description, it has been assumed that a silicon wafer is used for a substrate. However, it is needless to say that the invention can be equally applied to other various semiconductors.

I claim:

1. A method of measuring carrier distribution for determining a depthwise distribution of densities of carriers in a semiconductor wafer comprising steps of irradiating said semiconductor wafer with a linearly polarized monochromatic infrared light at an incident angle with respect to said semiconductor wafer, varying at least one of the wavelength and the incident angle of said light and measuring a change in polarization of light reflected from said semiconductor wafer to provide ellipsometric data on said incident and reflected lights from which ellipsometric data said depthwise distribution of densities of carriers is determined.

2. A method according to claim 1, wherein said changes in polarization of the reflected light are determined from a detection output of an infrared detector and an angular signal from a rotary encoder.

3. A method according to claim 1, wherein said wavelength is varied by successively changing set values in a monochromator for the wavelength with a mini-computer through an interface.

4. A method according to claim 1, wherein said incident angle is varied by rotating a rotatable stage with a mini-computer through an interface, said rotatable stage carrying said wafer.

5. A method according to claim 1, further comprising the step of determining which of predetermined calculated ellipsometric data on the incident and reflected lights for known carrier distributions most closely approximates said ellipsometric data provided by said measurement to determine said carrier distribution for said semiconductor wafer.

6. A carrier distribution measuring apparatus for determining a depthwise distribution of densities of carriers in a semiconductor wafer, comprising means for directing linearly polarized monochromatic infrared light to said semiconductor wafer with the incident angle or the wavelength of said infrared light being varied, means for detecting light reflected from the surface of said semiconductor wafer, and means for measuring changes of polarization of said reflected light to provide ellipsometric data on the incident and reflected light from which ellipsometric data said depthwise distribution of densities of carriers is determined.

7. A method of measuring carrier distribution for determining a depthwise distribution of densities of carriers in a semiconductor wafer comprising:

irradiating said semiconductor wafer with an incident linearly polarized monochromatic infrared light at an incident angle with respect to said semiconductor wafer, said incident light having s- and p-polarization components of an electric field represented, respectively, by $E_s$ and $E_p$;

varying at least one of the wavelength and the incident angle of said incident light;

measuring a change in polarization of light reflected from said semiconductor wafer, said reflected light having s- and p-polarization components of an electric field represented, respectively, by $E'_s$ and $E'_p$, to establish ellipsometric values for $\psi$ and $\Delta$ for the relationships:

$$\tan \psi = r_p/r_s \text{ and } \Delta = \phi_p - \phi_s$$

where $r_p$ and $r_s$ represent absolute values of complex reflection amplitudes of the p- and s-polarization components, respectively, and $\phi_p$ and $\phi_s$ represent, respectively, changes in the phase of the p- and s-components occurring upon reflection for establishing a relationship between said incident light and said reflected light of:

$$\begin{pmatrix} E'_s \\ E'_p \end{pmatrix} = \begin{pmatrix} r_s e^{i\phi_s} & 0 \\ 0 & r_p e^{i\phi_p} \end{pmatrix} \begin{pmatrix} E_s \\ E_p \end{pmatrix}$$

and comprising said established values of $\psi$ and $\Delta$ with predetermined values of $\psi$ and $\Delta$ corresponding to known carrier distributions to determined the carrier distribution of said irradiated semiconductor wafer.

* * * * *